United States Patent [19]
Ulrich et al.

[11] Patent Number: 6,077,336
[45] Date of Patent: Jun. 20, 2000

[54] AIR FILTER SYSTEM

[76] Inventors: Marcia A. Ulrich; Uwe J. Ulrich, both of 328 Clinton St., Lafayette, La. 70501

[21] Appl. No.: 09/115,862

[22] Filed: Jul. 15, 1998

[51] Int. Cl.[7] .................................................. B01D 46/44
[52] U.S. Cl. .................................. 96/222; 96/419; 96/424
[58] Field of Search ................................ 95/26, 285, 273; 55/DIG. 34, DIG. 31; 96/222, 424, 419, FOR 167, FOR 175

[56] References Cited

U.S. PATENT DOCUMENTS

| | | | |
|---|---|---|---|
| 4,065,262 | 12/1977 | Petrofff | 96/222 |
| 4,563,333 | 1/1986 | Frigon | 96/222 |
| 4,604,114 | 8/1986 | Ward | 96/222 |
| 4,875,912 | 10/1989 | Fulmer | 96/222 |
| 4,959,087 | 9/1990 | Kappernaros | 55/279 |
| 5,240,487 | 8/1993 | Kung | 55/486 |
| 5,240,653 | 8/1993 | Ramkissoon | 261/99 |
| 5,258,051 | 11/1993 | Anderson | 55/279 |
| 5,378,254 | 1/1995 | Maly et al. | 96/424 |
| 5,415,675 | 5/1995 | Powers et al. | 55/279 |
| 5,547,636 | 8/1996 | Vick et al. | 96/222 |
| 5,772,732 | 6/1998 | James et al. | 95/26 |
| 5,817,168 | 10/1998 | Wheless | 96/222 |

*Primary Examiner*—Duane S. Smith
*Attorney, Agent, or Firm*—Joseph N. Breaux

[57] ABSTRACT

An air filter system that includes a mechanism for notifying a user when a proper filter replacement period had elapsed that further includes a scenting mechanism for scenting the air flowing through the filter system with a pleasant odor. The air filter system includes a scent impregnated filter element held within a filter element frame provided with a user notification system and multiple scent impregnated strips.

4 Claims, 2 Drawing Sheets ized filter element frame provided with a user notification system and multiple scent impregnated strips; the filter element frame having an airflow window; the scent impregnated filter element being held within the filter element frame and across the air flow window of the filter element frame; the user notification mechanism being mounted to the filter element frame and including a digital control circuit, an on/off switch in connection with an on/off input of the digital control circuit, a pause switch in connection with a pause input of the digital control circuit, and a speaker in connection with a speaker output of the digital control circuit; the digital control circuit starting a first countdown period in response to an "on" signal at the on/off input; the digital control circuit generating a first sequence of speaker activation signals on the speaker output at a first predetermined interval upon expiration of the first countdown period; the first sequence of speaker activation signals lasting for a first sequence period in the absence of an "off" signal at the on/off input; the digital control circuit generating a second sequence of speaker activation signals on the speaker output at a second predetermined interval less than the first predetermined interval upon expiration of the first sequence period; the digital control circuit starting a second countdown period in response to receipt of a pause activation signal on the pause input; the second countdown period being shorter than the first countdown period; the digital control circuit generating a third sequence of speaker activation signals on the speaker output at the first predetermined interval upon expiration of the second countdown period; the third sequence of speaker activation signals lasting for a third sequence period in the absence of an "off" signal on the on/off input; the digital control circuit generating a fourth sequence of speaker activation signals on the speaker output at the second predetermined interval less than the first predetermined interval upon expiration of the third sequence period; the scent impregnated strips being positioned on side surfaces of the filter element frame; each scent impregnated foam strip being covered with a peel off cover strip.

AIR FILTER SYSTEM

TECHNICAL FIELD

The present invention relates to air filter systems and more particularly to an air filter system that includes a scent impregnated filter element held within a filter element frame provided with a user notification system and multiple scent impregnated strips; the filter element frame having an airflow window; the scent impregnated filter element being held within the filter element frame and across the air flow window of the filter element frame; the user notification mechanism being mounted to the filter element frame and including a digital control circuit, an on/off switch in connection with an on/off input of the digital control circuit, a pause switch in connection with a pause input of the digital control circuit, and a speaker in connection with a speaker output of the digital control circuit; the digital control circuit starting a first countdown period in response to an "on" signal at the on/off input; the digital control circuit generating a first sequence of speaker activation signals on the speaker output at a first predetermined interval upon expiration of the first countdown period; the first sequence of speaker activation signals lasting for a first sequence period in the absence of an "off" signal at the on/off input; the digital control circuit generating a second sequence of speaker activation signals on the speaker output at a second predetermined interval less than the first predetermined interval upon expiration of the first sequence period; the digital control circuit starting a second countdown period in response to receipt of a pause activation signal on the pause input; the second countdown period being shorter than the first countdown period; the digital control circuit generating a third sequence of speaker activation signals on the speaker output at the first predetermined interval upon expiration of the second countdown period; the third sequence of speaker activation signals lasting for a third sequence period in the absence of an "off" signal on the on/off input; the digital control circuit generating a fourth sequence of speaker activation signals on the speaker output at the second predetermined interval less than the first predetermined interval upon expiration of the third sequence period; the scent impregnated strips being positioned on side surfaces of the filter element frame; each scent impregnated foam strip being covered with a peel off cover strip.

BACKGROUND ART

Air filters are often positioned in the return air vent of air conditioning and heating systems to filter the air. These filters perform well when first installed, however, as more and more dust and debris accumulates in the filter, the filter can become clogged resulting in overworking of the other elements of the heating and air conditioning system as well as scenting the air with an unpleasant odor caused by filtering the air through the accumulation of dirt and other unpleasant smelling debris. It would be a benefit, therefore, to have a filter system that included a mechanism for notifying a user when a proper filter replacement period had elapsed. It would be a further benefit to have a filter system that included one or more scenting mechanisms for scenting the air flowing through the filter system with a pleasant odor.

GENERAL SUMMARY DISCUSSION OF INVENTION

It is thus an object of the invention to provide an air filter system that includes a mechanism for notifying a user when a proper filter replacement period had elapsed.

It is a further object of the invention to provide an air filter system that includes one or more scenting mechanisms for scenting the air flowing through the filter system with a pleasant odor.

It is a still further object of the invention to provide an air filter system that includes a scent impregnated filter element held within a filter element frame provided with a user notification system and multiple scent impregnated strips; the filter element frame having an airflow window; the scent impregnated filter element being held within the filter element frame and across the air flow window of the filter element frame; the user notification mechanism being mounted to the filter element frame and including a digital control circuit, an on/off switch in connection with an on/off input of the digital control circuit, a pause switch in connection with a pause input of the digital control circuit, and a speaker in connection with a speaker output of the digital control circuit; the digital control circuit starting a first countdown period in response to an "on" signal at the on/off input; the digital control circuit generating a first sequence of speaker activation signals on the speaker output at a first predetermined interval upon expiration of the first countdown period; the first sequence of speaker activation signals lasting for a first sequence period in the absence of an "off" signal at the on/off input; the digital control circuit generating a second sequence of speaker activation signals on the speaker output at a second predetermined interval less than the first predetermined interval upon expiration of the first sequence period; the digital control circuit starting a second countdown period in response to receipt of a pause activation signal on the pause input; the second countdown period being shorter than the first countdown period; the digital control circuit generating a third sequence of speaker activation signals on the speaker output at the first predetermined interval upon expiration of the second countdown period; the third sequence of speaker activation signals lasting for a third sequence period in the absence of an "off" signal on the on/off input; the digital control circuit generating a fourth sequence of speaker activation signals on the speaker output at the second predetermined interval less than the first predetermined interval upon expiration of the third sequence period; the scent impregnated strips being positioned on side surfaces of the filter element frame; each scent impregnated foam strip being covered with a peel off cover strip.

It is a still further object of the invention to provide an air filter system that accomplishes one of more of the above objects in combination.

Accordingly, an air filter system is provided. The air filter system includes a scent impregnated filter element held within a filter element frame provided with a user notification system and multiple scent impregnated strips; the filter element frame having an airflow window; the scent impregnated filter element being held within the filter element frame and across the air flow window of the filter element frame; the user notification mechanism being mounted to the filter element frame and including a digital control circuit, an on/off switch in connection with an on/off input of the digital control circuit, a pause switch in connection with a pause input of the digital control circuit, and a speaker in connection with a speaker output of the digital control circuit; the digital control circuit starting a first countdown period in response to an "on" signal at the on/off input; the digital control circuit generating a first sequence of speaker activation signals on the speaker output at a first predetermined interval upon expiration of the first countdown period; the first sequence of speaker activation signals lasting for a first sequence period in the absence of an "off" signal at the on/off input; the digital control circuit generating a second sequence of speaker activation signals on the speaker output at a second predetermined interval less than the first predetermined interval upon expiration of the first sequence period; the digital control circuit starting a second countdown period in response to receipt of a pause activation signal on the pause input; the second countdown period being shorter than the first countdown period; the digital control circuit generating a third sequence of speaker activation signals on the speaker output at the first predetermined interval upon expiration of the second countdown period; the third sequence of speaker activation signals lasting for a third sequence period in the absence of an "off" signal on the on/off input; the digital control circuit generating a fourth sequence of speaker activation signals on the speaker output at the second predetermined interval less than the first predetermined interval upon expiration of the third sequence period; the scent impregnated strips being positioned on side surfaces of the filter element frame; each scent impregnated foam strip being covered with a peel off cover strip.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

EXEMPLARY MODE FOR CARRYING OUT THE INVENTION

Figure 1:
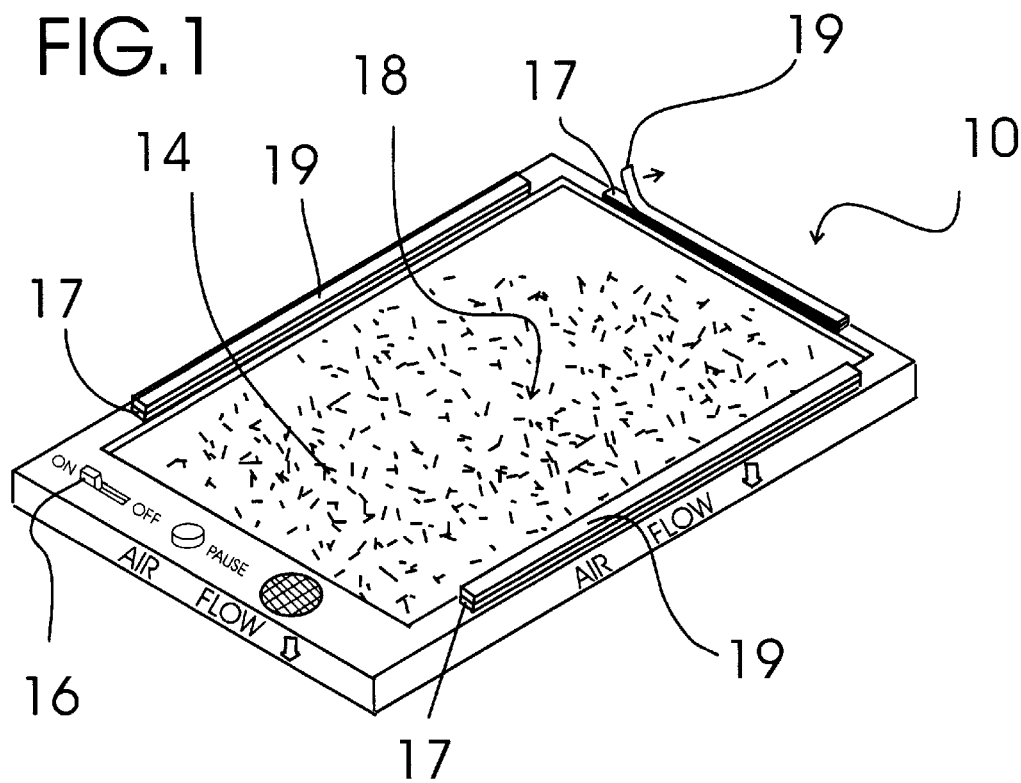
FIG. 1 is a perspective view of an exemplary embodiment of the air filter system of the present invention showing the front of the rectangular, cardboard filter element frame with the rectangular airflow window; the scent impregnated filter element held within the filter element frame and across the air flow window of the filter element frame; the user notification mechanism mounted to the filter element frame including the control circuit, the on/off switch, the pause switch, and the speaker; and three scent impregnated foam strips positioned on three side surfaces of the filter element frame, each scent impregnated foam strip being covered with a peel off cover strip.

FIG. 1 shows an exemplary embodiment of the air filter system of the present invention, generally designated by the numeral 10. Air filter system 10 includes a rectangular, cardboard filter element frame, generally designated 12; a scent impregnated, glass fiber filter element 14; a user notification mechanism, generally designated 16; and three scent impregnated foam strips 17. Scent impregnated foam strips 17 are positioned, respectively, on three side surfaces of filter element frame 12 and each is covered with a peel off cover strip 19. Use of three scent impregnated foam strips 17 allows the user to adjust the degree of air scenting when air filter system 10 is installed or, alternatively, to boost the scenting power of air filter system 10 after use reduces the scenting power of air filter element 14.

Figure 2:
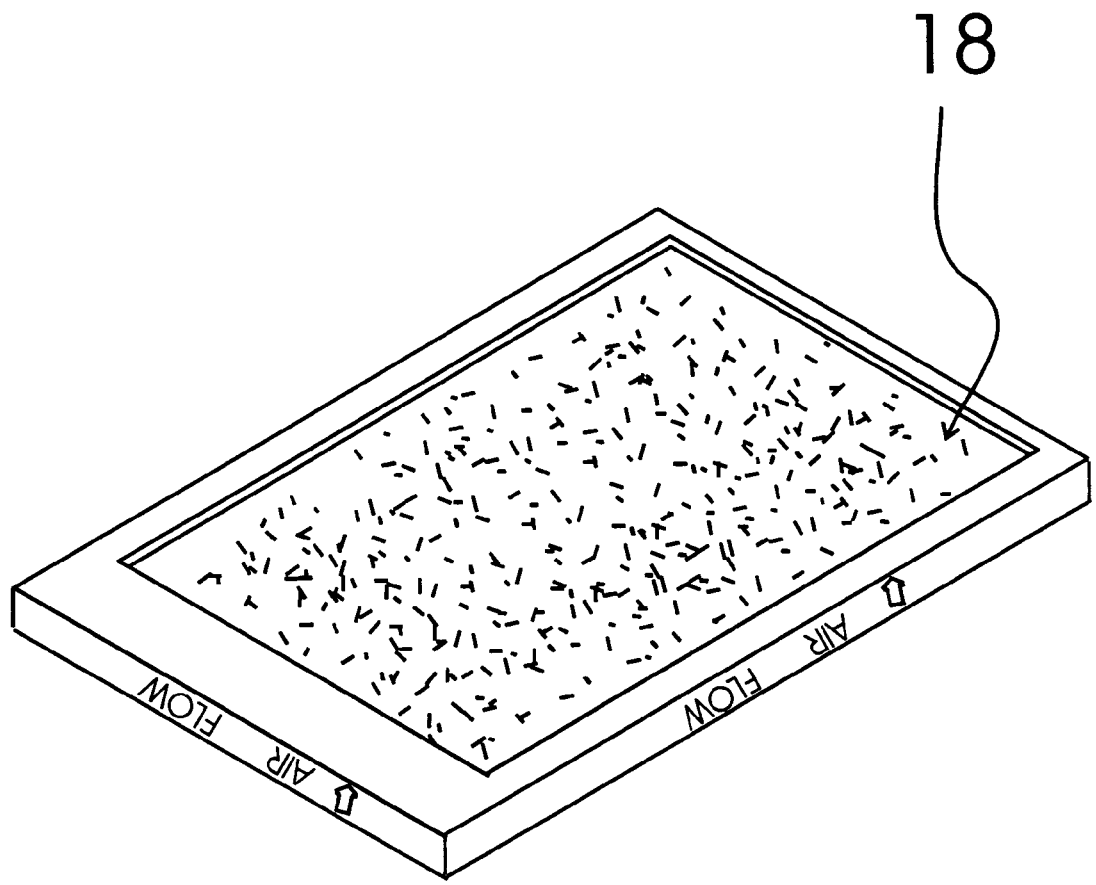
FIG. 2 is a perspective view of the exemplary air filter system of FIG. 1 showing the back of the rectangular, cardboard filter element frame with the rectangular airflow window; and the scent impregnated filter element held within the filter element frame and across the air flow window of the filter element frame.

Filter element frame 12 has a rectangular airflow window 18 formed through the front and, with reference to FIG. 2, the back side thereof. Scent impregnated filter element 14 is held within filter element frame 12 and across air flow window 18 in the conventional manner.

Figure 3:
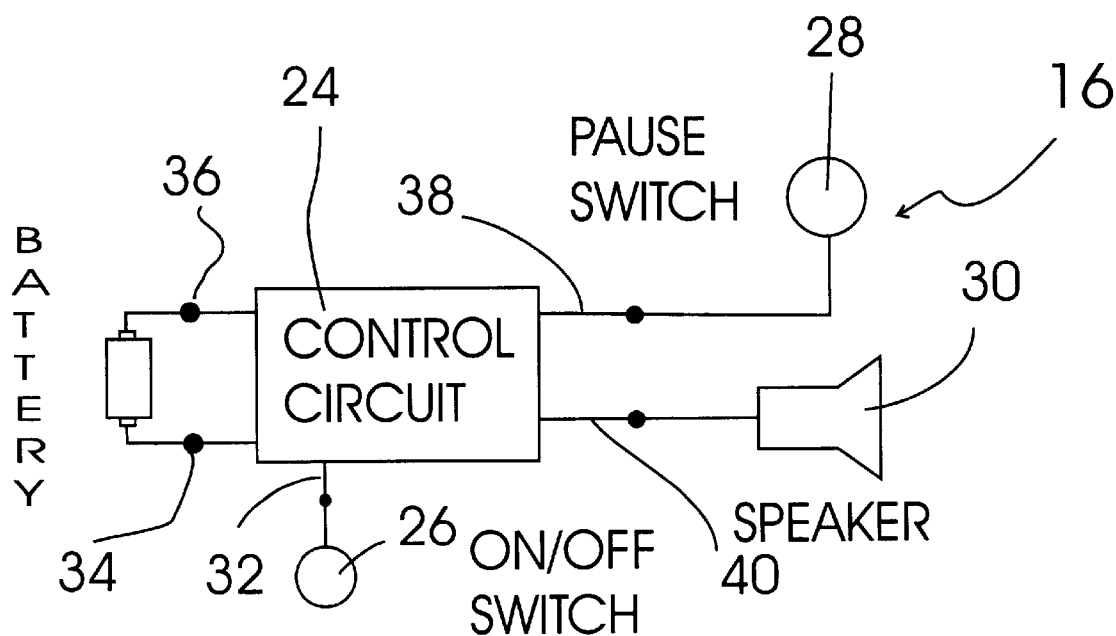
FIG. 3 is a schematic diagram of the user notification mechanism in isolation showing the digital control circuit, the two-position on/off switch, the momentary contact pause switch, and the speaker.

With reference to FIG. 3, user notification mechanism 16 is mounted to filter element frame 12 (FIG. 1) and includes a digital control circuit 24, a two-position on/off switch 26, a momentary contact pause switch 28, and a speaker 30. Digital control circuit 24 includes an on/off input 32; a positive battery terminal 34, a negative battery terminal 36, a pause input 38 and a speaker output 40. Digital control circuit 24 is a conventional microprocessor circuit programmed to operate as previously described with a first countdown period of thirty days, a first predetermined interval set at one hour, a first sequence period of two days, a second predetermined interval of one-half hour, a second countdown period of four days, and a third sequence period of two days.

With general reference to FIGS. 1–3, in use the user positions the filter system 10 into the filter holder of a heating and air conditioning system in place of an ordinary filter. The user then positions on/off switch 26 into the "on" position starting the first countdown period, in this embodiment thirty days. At the expiration of the first countdown period, control circuit 24 generates a first sequence of audible alarms at hourly intervals over a two day period to alert the user that air filter system 10 should be replaced. Should the user ignore this notification, the control circuit 24 then generates a second sequence of alarms at half hourly intervals until the user turns the on/off switch off or depresses pause switch 28. Depressing pause switch 28 sends a pause activation signal to pause input 38 causing control circuit 24 to begin a second count down period of four days to allow the user to obtain a replacement air filter system 10. After the second countdown period expires, control circuit 24 generates a third sequence of audible alarms at hourly intervals over a two day period to remind the user that the air filter system 10 should be replaced. Should the user ignore this reminder, the control circuit 24 then generates a fourth sequence of alarms at half hourly intervals until the user turns the on/off switch to the "off" position or depresses pause switch 28.

It can be seen from the preceding description that an air filter system has been provided that includes a mechanism for notifying a user when a proper filter replacement period had elapsed; that includes one or more scenting mechanisms for scenting the air flowing through the filter system with a pleasant odor; and that includes a scent impregnated filter element held within a filter element frame provided with a user notification system and multiple scent impregnated strips; the filter element frame having an airflow window; the scent impregnated filter element being held within the filter element frame and across the air flow window of the filter element frame; the user notification mechanism being mounted to the filter element frame and including a digital control circuit, an on/off switch in connection with an on/off input of the digital control circuit, a pause switch in connection with a pause input of the digital control circuit, and a speaker in connection with a speaker output of the digital control circuit; the digital control circuit starting a first countdown period in response to an "on" signal at the on/off input; the digital control circuit generating a first sequence of speaker activation signals on the speaker output at a first predetermined interval upon expiration of the first countdown period; the first sequence of speaker activation signals lasting for a first sequence period in the absence of an "off" signal at the on/off input; the digital control circuit generating a second sequence of speaker activation signals on the speaker output at a second predetermined interval less than the first predetermined interval upon expiration of the first sequence period; the digital control circuit starting a second countdown period in response to receipt of a pause activation signal on the pause input; the second countdown period being shorter than the first countdown period; the digital control circuit generating a third sequence of speaker activation signals on the speaker output at the first predetermined interval upon expiration of the second countdown period; the third sequence of speaker activation signals lasting for a third sequence period in the absence of an "off" signal on the on/off input; the digital control circuit generating a fourth sequence of speaker activation signals on the speaker output at the second predetermined interval less than the first predetermined interval upon expiration of the third sequence period; the scent impregnated strips being positioned on side surfaces of the filter element frame; each scent impregnated foam strip being covered with a peel off cover strip.

It is noted that the embodiment of the air filter system described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. An air filter system comprising:
   a filter element frame having an airflow window;
   a scent impregnated filter element held within said filter element frame;
   a user notification system mounted in connection with said filter element frame; and
   multiple scent impregnated strips positioned on side surfaces of said filter element frame; each of said multiple scent impregnated strips being covered with a peel off cover strip;
   said scent impregnated filter element being held within said filter element frame and across said air flow window of said filter element frame;
   said user notification mechanism including a digital control circuit, an on/off switch in connection with an on/off input of said digital control circuit, a pause switch in connection with a pause input of said digital control circuit, and a speaker in connection with a speaker output of said digital control circuit;
   said digital control circuit starting a first countdown period in response to an "on" signal at said on/off input;
   said digital control circuit generating a first sequence of speaker activation signals on said speaker output at a first predetermined interval upon expiration of said first countdown period;
   said first sequence of speaker activation signals lasting for a first sequence period in said absence of an "off" signal at said on/off input;
   said digital control circuit generating a second sequence of speaker activation signals on said speaker output at a second predetermined interval less than said first predetermined interval upon expiration of said first sequence period;
   said digital control circuit starting a second countdown period in response to receipt of a pause activation signal on said pause input;
   said second countdown period being shorter than said first countdown period;
   said digital control circuit generating a third sequence of speaker activation signals on said speaker output at said first predetermined interval upon expiration of said second countdown period;
   said third sequence of speaker activation signals lasting for a third sequence period in said absence of an "off" signal on said on/off input;
   said digital control circuit generating a fourth sequence of speaker activation signals on said speaker output at said second predetermined interval less than said first predetermined interval upon expiration of said third sequence period.

2. The air filter system of claim 1, wherein:
   said multiple scent impregnated strips are constructed of foam.

3. The air filter system of claim 1, wherein:
   said filter element frame is constructed of cardboard.

4. The air filter system of claim 1, wherein:
   said multiple scent impregnated strips are constructed of foam.

* * * * *